US00PP11748P2

(12) United States Plant Patent
Meilland

(10) Patent No.: US PP11,748 P2
(45) Date of Patent: Jan. 23, 2001

(54) FLORIBUNDA ROSE PLANT NAMED 'MEILYZRO'

(75) Inventor: Alain A. Meilland, Antibes (FR)

(73) Assignee: CP (Delaware), Inc., Wilmington, DE (US)

( * ) Notice: Under 35 U.S.C. 154(b), the term of this patent shall be extended for 0 days.

(21) Appl. No.: 09/210,910

(22) Filed: Dec. 15, 1998

(51) Int. Cl.[7] ..... A01H 5/00
(52) U.S. Cl. ..... Plt./150
(58) Field of Search ..... Plt./101, 108, 139, Plt./140, 150, 151

*Primary Examiner*—Howard J. Locker
(74) *Attorney, Agent, or Firm*—Burns, Doane, Swecker & Mathis, L.L.P.

(57) ABSTRACT

A new and distinct variety of rose plant of the Floribunda Class is provided which abundantly forms attractive double geranium red blossoms in the form of a well-balanced spray. The petals are slightly glossy in appearance. The buds are conical in configuration and are borne on long stems. An erect growth habit is exhibited. The foliage is dark green and contrasts nicely with the geranium red blossoms. The plant is well suited for the production of cut floral sprays under greenhouse growing conditions.

1 Drawing Sheet

SUMMARY OF THE INVENTION

Figures 1, 2, 3, 4, 5, 6, 7, 8, 9, 10, 11, 12, 13, 14, 15, 16, 17:
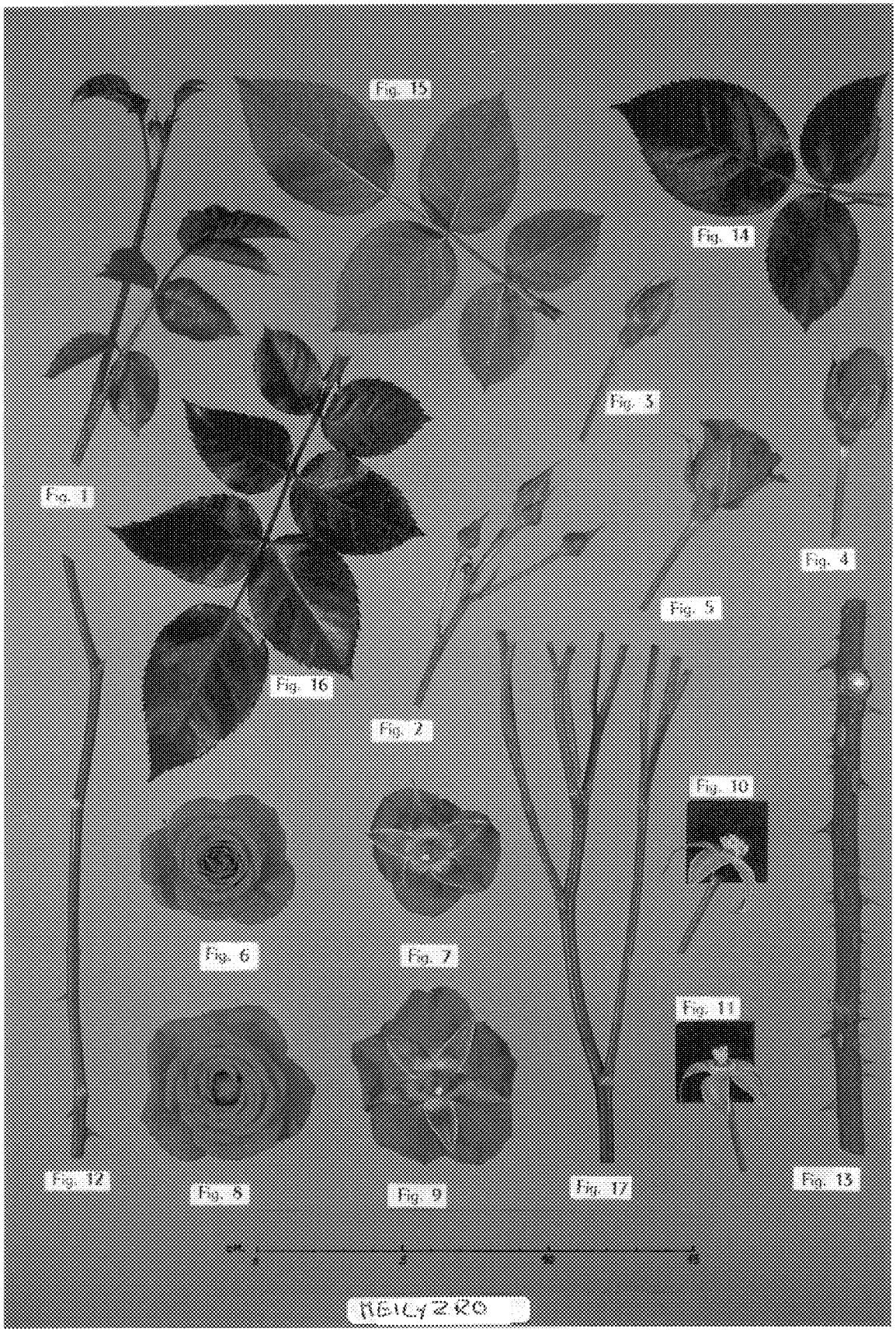

The new variety of (*Rosa hybrida*) Floribunda rose plant was created by artificial pollination wherein two parents were crossed which previously had been studied in the hope that they would contribute the desired characteristics. The female parent (i.e., the seed parent) of the new variety was the product of the pollination of the 'Keinoumi' variety (U.S. Plant Pat. No. 8,484) and the 'Olijdum' variety (non-patented in the United States). The male parent (i.e., the pollen parent) of the new variety was the 'Meikister' variety (U.S. Plant Pat. No. 8,267). The parentage of the new variety can be summarized as follows:

('Keinoumi'×'Olijdum')×'Meikister'.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms conical buds on long stems in the form of a spray, (b) forms in abundance attractive geranium red blossoms, (c) exhibits an erect growth habit, and (d) forms attractive semi-glossy dark green foliage.

The blossom petals are slightly glossy in appearance. Also, the spray inflorescence is well balanced, and its geranium red coloration contrasts nicely with the dark green foliage.

The new variety well meets the needs of the horticultural industry. It is particularly well-suited for use in the production of cut floral sprays under greenhouse growing conditions.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the 'Meilyzro' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age were observed during March while growing on *Rosa indica* understock in greenhouses at LeCannet des Maures, Var, France.

FIG. 1—illustrates a specimen of a young shoot;

FIG. 2—illustrates a specimen of a group of floral buds before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower — plan view — obverse;

FIG. 7—illustrates a specimen of an open flower — plan view — reverse;

FIG. 8—illustrates a specimen of a fully open flower — plan view — obverse;

FIG. 9—illustrates a specimen of a fully open flower — plan view — reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets — plan view — upper surface;

FIG. 15—illustrates a specimen of a leaf with five leaflets — plan view — under surface;

FIG. 16—illustrates a specimen of a leaf with seven leaflets — plan view — upper surface; and FIG. 17—illustrates a specimen multiply-branched stem capable of bearing a floral spray.

DETAILED DESCRIPTION

The chart used in the identification of the colors is that of The Royal Horticultural Society (R.H.S. Colour Chart). When more common color terms are utilized they are to be accorded customary dictionary significance. The description is based on two year-old specimens of the new variety which were observed during March while budded on *Rosa indica* understock and growing in greenhouses at LeCannet des Maures, Var, France. Dimensions in centimeters are provided at the bottom of the photograph. The new variety of the present invention has not been tested to date while growing outdoors.

Class: Floribunda

Plant:

*Height*.—A plant pruned to a height of 85 cm. commonly produces floral stems having a length of approximately 50 to 70 cm.

*Habit*.—Erect.

Branches:

*Color*.—Young stems: Near Green Group 138A. Adult wood: Near Green Group 137B.

*Thorns*.—Size: Medium (as illustrated). Quantity: Medium (as illustrated). Configuration: Lightly concave with a narrow base on the under surface. Color: Greyed-Red Group 178B on young stems and Greyed-Orange Group 175D on adult wood.

Leaves:

*Petioles*.—Somewhat glandular on the upper surface.

*Stipules*.—Adnate, pectinate, and narrow.

*Leaflets*.—Number: 3, 5 (most often), and 7. Size: Approximately 12 cm in length and approximately 9 cm in width. Shape: Elliptic. Texture: Moderately firm. Serration: Regular. General appearance: Dense, dark green, and semi-glossy. Color (young foliage): Upper surface: Green Group 139A. Young shoots and foliage include strong anthocyanin coloration. Under surface: Greyed-Green Group 191A. Color (adult foliage): Upper surface: Near Green Group 137A. Under surface: Near Yellow-Green Group 191A.

Inflorescence:

*Number of flowers*.—Commonly approximately 6 to 15 per stem.

*Peduncle*.—Light green, Yellow-Green Group 143A, in coloration, with many prickles and the length is approximately 5 to 8 cm. on average.

*Sepals*.—Upper surface: Tomentose, Green Group 138A in coloration, and commonly with two small extensions on one of the five sepals. Under surface: Somewhat glandular.

*Buds*.—Shape: Conical. Length: Approximately 3 cm. on average. Size: Medium for class. Color upon opening: Upper surface: Near Red Group 45B, and on the external petals there is a small veinlet which is bordered with white on up to approximately two-thirds of the petals. Under surface: Near Red Group 46A.

*Flower*.—Form: Flattened. Diameter: Approximately 6 cm. on average. Color (when opening begins): Upper surface: Near Red Group 45B, and on the external petals there is a small veinlet bordered with white on up to approximately two-thirds of the petals. Under surface: Near Red Group 46A. Color (when blooming): Upper surface: Near Red Group 44A, and on the external petals there is a small veinlet bordered with white on up to approximately two-thirds of the petals. Under surface: Near Red Group 45A. Color (at end of opening): Upper surface: Near Red Group 44B, and on the external petals there is a small veinlet bordered with white on up to approximately two-thirds of the petals. Under surface: Near Red Group 46B. Fragrance: None. Petal Number: Approximately 35 on average. Petal configuration: With a reflexed tip and a rounded base as illustrated. Petal drop: Very good, the petals commonly detach cleanly. Anthers: Tan in coloration. Stamen number: Approximately 57 on average. Filaments: Pinkish in coloration. Pistil number: Approximately 128 on average. Stigmas: Greenish light yellow in coloration. Styles: Whitish in coloration. Receptacle: Light green in coloration, and in longitudinal section in the shape of a pitcher. Hips: Substantially round hips are formed. Lasting quality: Approximately 12 to 14 days on the plant, and approximately 10 to 12 days when cut and placed in a vase.

Development

*Vegetation*.—Very strong.

*Blooming*.—Very abundant.

*Resistance to diseases*.—Very good.

I claim:

1. A new and distinct variety of Floribunda rose plant characterized by the following combination of characteristics:

(a) forms conical buds on long stems in the form of a spray, (b) forms in abundance attractive geranium red blossoms, (c) exhibits an erect growth habit, and (d) forms attractive semi-glossy dark green foliage;

substantially as herein shown and described.

* * * * *

REICZKO